United States Patent
Blackwell et al.

(10) Patent No.: US 8,389,597 B2
(45) Date of Patent: *Mar. 5, 2013

(54) HIGH WATER CONTENT OPHTHALMIC DEVICES

(75) Inventors: Richard I. Blackwell, Katy, TX (US); Joseph C. Salamone, San Antonio, TX (US); Jay F. Kunzler, Canandaigua, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/370,364

(22) Filed: Feb. 10, 2012

(65) Prior Publication Data

US 2012/0141408 A1    Jun. 7, 2012

Related U.S. Application Data

(63) Continuation of application No. 12/350,262, filed on Jan. 8, 2009, now Pat. No. 8,138,290.

(60) Provisional application No. 61/023,459, filed on Jan. 25, 2008.

(51) Int. Cl.
    *G02B 1/04*    (2006.01)

(52) U.S. Cl. ........ 523/106; 523/105; 523/107; 523/108; 526/303.1

(58) Field of Classification Search .................. 523/106, 523/105, 107, 108; 526/303.1
    See application file for complete search history.

(56) References Cited

U.S. PATENT DOCUMENTS

| | | | |
|---|---|---|---|
| 4,910,277 A | 3/1990 | Bambury et al. | |
| 5,070,215 A | 12/1991 | Bambury et al. | |
| 5,270,418 A | 12/1993 | Kunzler et al. | |
| 5,298,533 A | 3/1994 | Nandu et al. | |
| 6,245,830 B1 | 6/2001 | Benz et al. | |
| 6,517,933 B1 | 2/2003 | Soane et al. | |
| 6,627,674 B2 | 9/2003 | Benz et al. | |
| 6,992,118 B2 | 1/2006 | Sulc et al. | |
| 8,138,290 B2 * | 3/2012 | Blackwell et al. | 526/303.1 |
| 2002/0055551 A1 | 5/2002 | Benz et al. | |
| 2002/0058724 A1 | 5/2002 | Benz et al. | |
| 2003/0044468 A1 | 3/2003 | Cellesi et al. | |

FOREIGN PATENT DOCUMENTS

WO    WO99/11692    3/1999

OTHER PUBLICATIONS

Zisman et al., "Oleophobic Monolayers," J. Colloid Sci., p. 513-538, (Jan. 7, 1946).
International Search Report (PCT/ISA/210) and Written Opinion (PCT/ISA/237) mailed on Jun. 16, 2009.

* cited by examiner

*Primary Examiner* — Edward Cain
(74) *Attorney, Agent, or Firm* — Glenn D. Smith

(57) ABSTRACT

An ophthalmic device is disclosed that is a polymerization product of a monomeric mixture comprising (a) a major amount of a non-silicone-containing hydrophilic monomer; (b) a hydrophobic monomer; and (c) a crosslinking agent, wherein the ophthalmic device has an equilibrium water content of at least about 70 weight percent and further wherein the ophthalmic device has an evaporative dehydration barrier layer on the surface thereof. A method for the mitigation of evaporative corneal dehydration employing the high water content ophthalmic device is also disclosed.

21 Claims, 1 Drawing Sheet

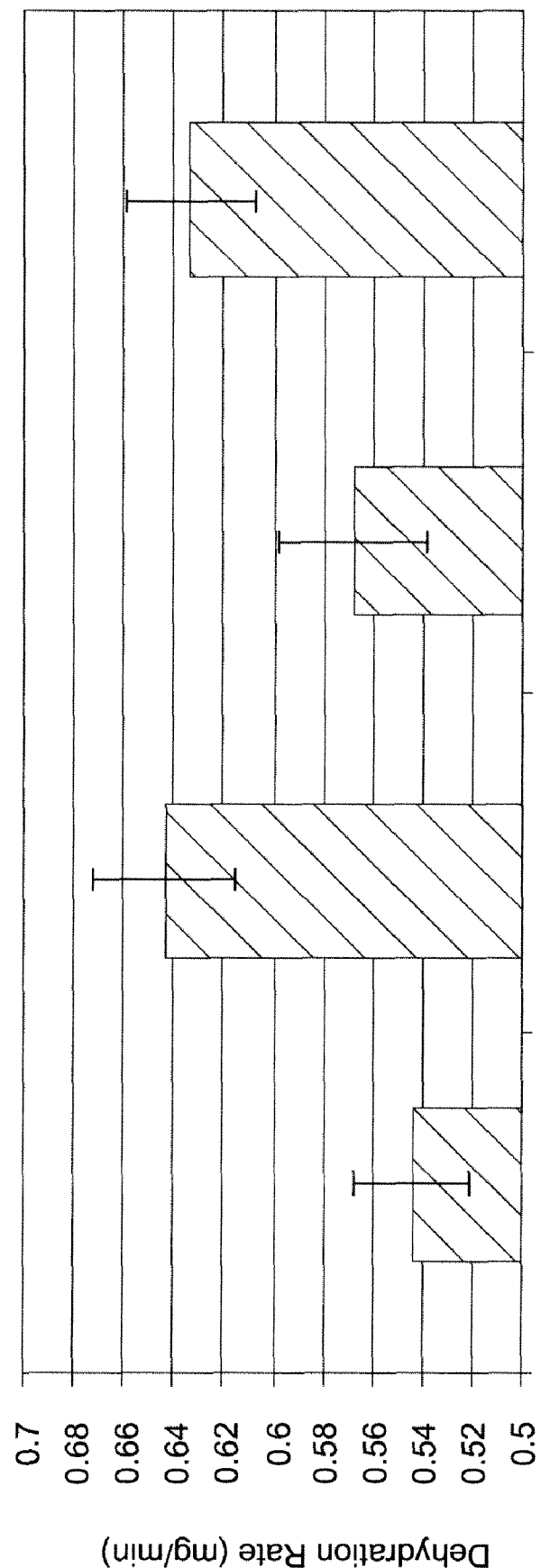

HIGH WATER CONTENT OPHTHALMIC DEVICES

PRIORITY CLAIMS TO PRIOR APPLICATIONS

This application is a continuation of application Ser. No. 12/350,262 filed Jan. 8, 2009, which claims the benefit of Provisional Patent Application No. 61/023,459 filed Jan. 25, 2008, the contents of both of which are incorporated by reference herein.

BACKGROUND OF THE INVENTION

1. Technical Field

The present invention generally relates to ophthalmic devices such as contact lenses having a high water content with improved evaporative dehydration.

2. Description of the Related Art

Soft contact lenses have been available since the 1980s. It is important that contact lenses be comfortable and safe to wear. However, while there are many people who can successfully wear contact lenses, there are a number of people who can wear contact lenses for only a short period of time due to, for example, contact lens related dry eye. Symptoms of this disorder include, for example, thin and/or unstable tear films, corneal staining and subjective symptoms such as ocular discomfort, burning/stinging and dryness. Contact lens wear may trigger the onset of these symptoms or may exacerbate the symptoms.

Although lenses with high water contents are softer, more lubricious and more comfortable to wear, such lenses may not have one or more properties useful to provide comfortable and safe wearing of the contact lenses. For example, a particular problem associated with high water content contact lenses is evaporative corneal dehydration. As free water in the lens is lost due to evaporation, it is replaced with water from the cornea. Evaporative water loss at the anterior lens surface is a potential cause of contact lens dehydration and of post-lens tear-film depletion, which in turn, may lead to discomfort, dry eye, corneal staining and/or other damage to the eye. Dehydration of the epithelium results in corneal damage and therefore corneal staining. This staining is usually limited to the superficial 2 to 3 layers of the epithelium and spread over the inferior portion of the cornea, but if the stimulus is sufficiently great, damage can be deep and severe allowing rapid diffusion of fluorescein into the stroma. The staining can occur rapidly within a few hours of lens insertion but can take 4 to 6 hours or more.

Historically, high water content contact lenses were typically made by lathing the high water content lens from a cylindrical blank of polymerized lens material (cylindrical blanks are commonly referred to as a "button"). For example, the high water content contact lenses are made by (a) polymerizing the initial monomeric mixture in tubes to provide rod-shaped articles, (b) cutting the rods into buttons, and (c) lathing the buttons into contact lenses. However, a surface of a lens produced from lathed buttons can be quite different from the surface of a lens cast from molds.

U.S. Pat. No. 6,245,830 discloses a high water content and high water balance contact lens made of a homopolymer or copolymer having more than 80 mole percent and preferably more than 90 mol percent of 2,3-dihydroxypropyl methacrylate (GMA) and up to 20 mol percent, generally from 0.05 up to 10 mol percent of a reactive pyrrolidone such as N-vinyl pyrrolidone.

U.S. Pat. No. 6,627,674 ("the '674 patent") discloses a high water content and high water balance contact lens made of a homopolymer or copolymer having more than 80 mole percent and preferably more than 90 mol percent of GMA and having an equilibrium water content of at least about 60 percent by weight and the contact lens has a water balance of more than about 8 relative to poly(2-hydroxyethyl methacrylate). The '674 patent further discloses that GMA polymers can be polymerized in the presence of a reactive polar aprotic diluent, such as N-vinyl pyrrolidone and/or a non-reactive polar aprotic diluent.

There remains a need for a high water content contact lens possessing superior dimensional stability and having a low rate of dehydration such that evaporative corneal dehydration can be reduced.

SUMMARY OF THE INVENTION

In accordance with one embodiment of the present invention, an ophthalmic device is provided that is a polymerization product of a monomeric mixture comprising: (a) a major amount of a non-silicone-containing hydrophilic monomer; (b) a hydrophobic monomer; and (c) a crosslinking agent, wherein the ophthalmic device has an equilibrium water content of at least about 70 weight percent and further wherein the surface of the ophthalmic device substantially inhibits evaporative dehydration.

In accordance with a second embodiment of the present invention, an ophthalmic device is provided that is a polymerization product of a monomeric mixture comprising: (a) a major amount of a non-silicone-containing hydrophilic monomer; (b) a hydrophobic monomer; and (c) a crosslinking agent, wherein the ophthalmic device has an equilibrium water content of at least about 70 weight percent and further wherein the ophthalmic device exhibits a dehydration rate of less than or equal to about 0.600 mg/minute.

In accordance with a third embodiment of the present invention, a method is provided comprising the step of casting a monomeric mixture comprising (a) a major amount of a non-silicone-containing hydrophilic monomer; (b) a hydrophobic monomer; and (c) a crosslinking agent n a hydrophobic substrate to form an ophthalmic device having an evaporative dehydration barrier layer on the surface thereof and wherein the ophthalmic device has an equilibrium water content of at least about 70 weight percent.

In accordance with a fourth embodiment of the present invention, a method for substantially mitigating evaporative corneal dehydration associated with an ophthalmic device having an equilibrium water content of at least about 70 weight percent is provided comprising contacting an eye of a subject with an ophthalmic device that is a polymerization product of a monomeric mixture comprising: (a) a major amount of a non-silicone-containing hydrophilic monomer; (b) a hydrophobic monomer; and (c) a crosslinking agent, wherein the ophthalmic device has an equilibrium water content of at least about 70 weight percent and further wherein the ophthalmic device has an evaporative dehydration barrier layer on the surface thereof.

The term "subject" or "a patient" or "a host" as used herein refers to mammalian animals, preferably human.

The term "mitigating" as used herein shall be understood to mean (1) preventing or delaying the appearance of one or more clinical symptoms of the evaporative corneal dehydration developing in a subject that may be afflicted with evaporative corneal dehydration but does not yet experience or display symptoms of evaporative corneal dehydration, (2) inhibiting evaporative corneal dehydration, i.e., arresting or reducing the development of evaporative corneal dehydration in a subject, or (3) relieving evaporative corneal dehydration, i.e., causing regression of evaporative corneal dehydration in a subject.

The high water content ophthalmic devices of the present invention advantageously mitigate evaporative corneal dehydration in an eye of a subject by possessing an evaporative dehydration barrier layer on the surface of the device. In this manner, the device can be worn in the eye for an extended period of time with long term corneal health to the cornea of the eye. The evaporative dehydration barrier layer is formed by polymerizing (a) a major amount of a non-silicone-containing hydrophilic monomer; (b) a hydrophobic monomer; and (c) a crosslinking agent against a hydrophobic substrate such that the hydrophobic monomer is driven to the surface of the device resulting in a evaporative dehydration barrier layer on the surface of the device.

BRIEF DESCRIPTION OF THE DRAWING

FIG. 1 is a graph illustrating the rate of dehydration of the contact lens of Example 1 versus commercially available contact lenses.

DETAILED DESCRIPTION OF THE PREFERRED EMBODIMENTS

The present invention is directed to high water content ophthalmic devices. Although the invention is applicable to a variety of high water content ophthalmic devices, the invention is especially useful and advantageous for high water content contact lenses. As used herein, the terms "ophthalmic device" and "lens" refer to devices that reside in or on the eye. These devices can provide optical correction, wound care, drug delivery, diagnostic functionality or cosmetic enhancement or any combination of these properties. Representative examples of such devices include, but are not limited to, soft contact lenses, e.g., soft, hydrogel lenses, soft, non-hydrogel lenses and the like, hard contact lenses, e.g., hard, gas permeable lens materials and the like, intraocular lenses, overlay lenses, ocular inserts, optical inserts and the like. As is understood by one skilled in the art, a lens is considered to be "soft" if it can be folded back upon itself without breaking. The high water content ophthalmic devices such as high water content contact lenses of the present invention can be spherical, toric, bifocal, may contain cosmetic tints, opaque cosmetic patterns, combinations thereof and the like.

The high water content ophthalmic devices of the present invention will have an equilibrium water content of at least about 70 weight percent. In one embodiment, the high water content ophthalmic devices of the present invention will have an equilibrium water content of at least about 80 weight percent. The high water content ophthalmic devices are a polymerization product of a monomeric mixture including at least (a) a major amount of a non-silicone-containing hydrophilic monomer; (b) a hydrophobic monomer; and (c) a crosslinking agent.

Suitable non-silicone-containing hydrophilic monomers include amides such as N,N-dimethylacrylamide, N,N-dimethylmethacrylamide and the like, cyclic lactams such as N-vinyl-2-pyrrolidone and the like, poly(alkene glycols) functionalized with polymerizable groups and the like. Examples of useful functionalized poly(alkene glycols) include poly(diethylene glycols) of varying chain length containing monomethacrylate or dimethacrylate end caps. In a preferred embodiment, the poly(alkene glycol) polymer contains at least two alkene glycol monomeric units. Still further examples are the hydrophilic vinyl carbonate or vinyl carbamate monomers disclosed in U.S. Pat. No. 5,070,215, and the hydrophilic oxazolone monomers disclosed in U.S. Pat. No. 4,910,277. Other suitable hydrophilic monomers will be apparent to one skilled in the a t. Mixtures of the foregoing non-silicone-containing hydrophilic monomers can also be used in the monomeric mixtures herein.

The hydrophilic monomers such as a N-vinyllactam-containing monomer are present in the monomeric mixture in a major amount, e.g., an amount greater than or equal to about 70 weight percent and preferably greater than or equal to about 80 weight percent, based on the total weight of the monomeric mixture.

Suitable hydrophobic monomers (b) include ethylenically unsaturated hydrophobic monomers such as, for example, (meth)acrylates-containing hydrophobic monomers, N-alkyl (meth)acrylamides-containing hydrophobic monomers, alkyl vinylcarbonates-containing hydrophobic monomers, alkyl vinylcarbamates-containing hydrophobic monomers, fluoroalkyl(meth)acrylates-containing hydrophobic monomers, N-fluoroalkyl(meth)acrylamides-containing hydrophobic monomers, N-fluoroalkyl vinylcarbonates-containing hydrophobic monomers, N-fluoroalkyl vinylcarbamates-containing hydrophobic monomers, silicone-containing (meth)acrylates-containing hydrophobic monomers, (meth)acrylamides-containing hydrophobic monomers, vinyl carbonates-containing hydrophobic monomers, vinyl carbamates-containing hydrophobic monomers, styrenic-containing hydrophobic monomers, polyoxypropylene(meth)acrylate-containing hydrophobic monomers and the like and mixtures thereof. As used herein, the term "(meth)" denotes an optional methyl substituent. Thus, terms such as "(meth)acrylate" denotes either methacrylate or acrylate, and "(meth)acrylamide" denotes either methacrylamide or acrylamide.

In a preferred embodiment, a hydrophobic monomer is represented by Formula I:

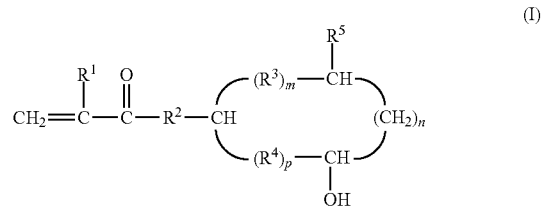

wherein $R^1$ is methyl or hydrogen; $R^2$ is —O— or —NH—; $R^3$ and $R^4$ are independently a divalent radical selected from the group consisting of —$CH_2$—, —CHOH— and —$CHR^6$—; $R^5$ and $R^6$ are independently a branched $C_3$-$C_8$ alkyl group; and n is an integer of at least 1, and m and p are independently 0 or an integer of at least 1, provided that the sum of m, p and n is 2, 3, 4 or 5. Representative examples of hydrophobic monomers (b) include, but are not limited to, 4-t-butyl-2-hydroxycyclohexyl methacrylate (TBE); 4-t-butyl-2-hydroxycyclopentyl methacrylate; 4-t-butyl-2-hydroxycyclohexyl methacrylamide (TBA); 6-isopentyl-3-hydroxycyclohexyl methacrylate; and 2-isohexyl-5-hydroxycyclopentyl methacrylamide. Preferred hydrophobic monomers (b) include compounds of formula I wherein $R^3$ is —$CH_2$—, m is 1 or 2, p is 0, and the sum of m and n is 3 or 4. TBE and TBA are especially preferred.

The hydrophobic monomer will ordinarily be present in the monomeric mixture in an amount ranging from about 0.5 to about 25 and preferably from about 1 to about 10 weight percent, based on the total weight of the monomeric mixture.

Suitable crosslinking agents for use herein are known in the art. A useful crosslinking monomer can have at least two polymerizable functional groups. Representative crosslinking agents include, but are not limited to, allyl methacrylate and ethylene glycol dimethyacrylate (EGDMA). The crosslinking agent is generally used in amounts of from about 0.1 to about 5 weight percent, and generally less than about 2 weight percent, based on the total weight of the monomeric mixture.

It is particularly advantageous to employ a hydrophobic silicon-containing monomer in addition to or in place of the hydrophobic monomers discussed hereinabove. It is particularly advantageous to employ a hydrophobic silicon-containing monomer possessing a sufficient degree of hydrophilicity such that the hydrophobic silicon containing monomer is compatible in the monomeric mixture. Suitable hydrophobic silicon-containing monomers include end terminal functionalized trialkoxy silanes such as a trialkoxy silane having a polymerizable ethylenically unsaturated-containing terminal group. A representative example of an end terminal functionalized trialkoxy silane is represented by general Formula II:

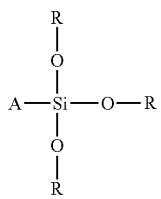
(II)

wherein each R independently denotes a lower $C_1$-$C_{12}$ alkyl radical such as methyl, ethyl and the like, substituted or unsubstituted $C_6$-$C_{12}$ aryl radical such as a phenyl radical or a group represented by

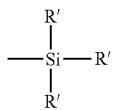

wherein each R' independently denotes a lower $C_1$-$C_{12}$ alkyl radical or a substituted or unsubstituted $C_6$-$C_{12}$ aryl radical and A is independently a polymerizable ethylenically unsaturated-containing radical. Representative examples of a "polymerizable ethylenically unsaturated-containing radical" include, by way of example, (meth)acrylate-containing radicals, (meth)acrylamide-containing radicals, vinylcarbonate-containing radicals, vinylcarbamate-containing radicals, styrene-containing radicals, vinyl radicals, vinyl ether radicals, maleimide radicals, itaconate radicals, fumarate radicals and the like. In one embodiment, a polymerizable ethylenically unsaturated-containing radical is represented by general Formula III:

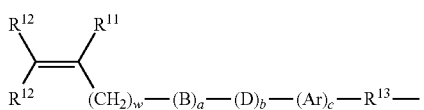
(III)

wherein $R^{11}$ is hydrogen or methyl;

each $R^{12}$ is independently hydrogen, an alkyl radical having 1 to 6 carbon atoms, or a —CO—Y—$R^{14}$ radical wherein Y is —O—, —S— or —NH— and $R^{14}$ is an alkyl radical having 1 to about 10 carbon atoms;

$R^{13}$ is a divalent alkenyl radical having 1 to about 12 carbon atoms;

B denotes —O— or —NH—; D denotes —CO—, —OCO— or —COO;

Ar denotes an aromatic radical having 6 to about 30 carbon atoms;

w is 0 to 6; a is 0 or 1; b is 0 or 1; and c is 0 or 1.

Representative examples of hydrophobic silicon-containing monomers include those of the Formulae IV-VI:

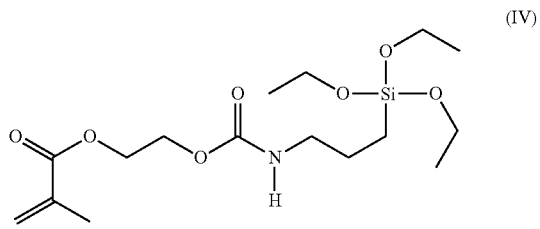
(IV)

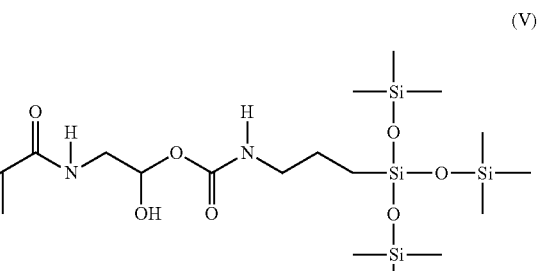
(V)

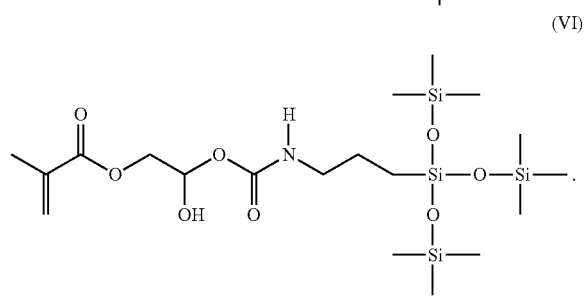
(VI)

The hydrophobic silicon-containing monomer will ordinarily be present in the monomeric mixture in an amount ranging from about 0.5 to about 25 weight percent and preferably from about 1 to about 10 weight percent, based on the total weight of the monomeric mixture.

If desired, an end terminal functionalized surfactant can be included in the monomer mixture. A suitable end terminal functionalized surfactant includes, by way of example, one or more end terminal functionalized polyethers. Useful polyethers to be end terminal functionalized comprise one or more chains or polymeric components which have one or more (—O—R—) repeats units wherein R is an alkylene or arylene group having 2 to about 6 carbon atoms. The polyethers may be derived from block copolymers formed from different ratio components of ethylene oxide (EO) and propylene oxide (PO). Such polyethers and their respective component segments may include different attached hydrophobic and hydrophilic chemical functional group moieties and segments.

A representative example of a suitable polyether which can be end terminal functionalized is a poloxamer block copolymer. One specific class of poloxamer block copolymers are those available under the trademark Pluronic (BASF Wyandotte Corp., Wyandotte, Mich.). Poloxamers include Pluronics and reverse Pluronics. Pluronics are a series of ABA block copolymers composed of poly(ethylene oxide)-poly(propylene oxide)-poly(ethylene oxide) blocks as generally represented in Formula VII:

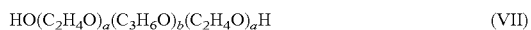
$$HO(C_2H_4O)_a(C_3H_6O)_b(C_2H_4O)_aH \quad \text{(VII)}$$

wherein a is independently at least 1 and b is at least 1.

Reverse Pluronics are a series of BAB block copolymers, respectively composed of poly(propylene oxide)-poly(ethylene oxide)-poly(propylene oxide) blocks as generally represented in Formula VIII:

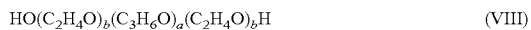
$$HO(C_2H_4O)_b(C_3H_6O)_a(C_2H_4O)_bH \quad \text{(VIII)}$$

wherein a is at least 1 and b is independently at least 1. The poly(ethylene oxide), PEO, blocks are hydrophilic, whereas the poly(propylene oxide), PPO, blocks are hydrophobic in nature. The poloxamers in each series have varying ratios of PEO and PPO which ultimately determines the hydrophilic-lipophilic balance (HLB) of the material, i.e., the varying HLB values are based upon the varying values of a and b, a representing the number of hydrophilic poly(ethylene oxide) units (PEO) being present in the molecule and b representing the number of hydrophobic poly(propylene oxide) units (PPO) being present in the molecule.

Poloxamers and reverse poloxamers have terminal hydroxyl groups that can be terminal functionalized. An example of a terminal functionalized poloxamer and as discussed hereinbelow is poloxamer dimethacrylate (e.g., Pluronic® F127 dimethacrylate) as disclosed in U.S. Patent Application Publication No. 2003/0044468. Other examples include glycidyl-terminated copolymers of polyethylene glycol and polypropylene glycol as disclosed in U.S. Pat. No. 6,517,933.

Another example of a suitable polyether which can be end terminal functionalized is a poloxamine block copolymer. While the poloxamers and reverse poloxamers are considered to be difunctional molecules (based on the terminal hydroxyl groups), the poloxamines are in a tetrafunctional form, i.e., the molecules are tetrafunctional block copolymers terminating in primary hydroxyl groups and linked by a central diamine. One specific class of poloxamine block copolymers are those available under the trademark Tetronic (BASF). Poloxamines include Tetronic and reverse Tetronics. Poloxamines have the following general structure of Formula IX:

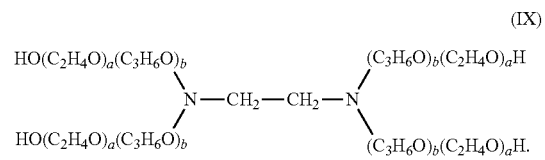

wherein a is independently at least 1 and b is independently at least 1.

The poloxamer and/or poloxamine is functionalized to provide the desired reactivity at the end terminal of the molecule. The functionality can be varied and is determined based upon the intended use of the functionalized PEO- and PPO-containing block copolymers. That is, the PEO- and PPO-containing block copolymers are reacted to provide end terminal functionality that is complementary with the intended device forming monomer mixture. The term block copolymer as used herein shall be understood to mean a poloxamer and/or poloxamine as having two or more blocks in their polymeric backbone(s).

Generally, selection of the functional end group is determined by the functional group of the reactive molecule(s) in the monomer mix. For example, if the reactive molecule contains a carboxylic acid group, glycidyl methacrylate can provide a methacrylate end group. If the reactive molecule contains hydroxy or amino functionality, isocyanato ethyl methacrylate or (meth)acryloyl chloride can provide a methacrylate end group and vinyl chloro formate can provide a vinyl end group. A wide variety of suitable combinations of ethylenically unsaturated end groups and reactive molecules will be apparent to those of ordinary skill in the art. For example, the functional group may comprise a moiety selected from amine, hydrazine, hydrazide, thiol (nucleophilic groups), carboxylic acid, carboxylic ester, including imide ester, orthoester, carbonate, isocyanate, isothiocyanate, aldehyde, ketone, thione, alkenyl, acrylate, methacrylate, acrylamide, sulfone, maleimide, disulfide, iodo, epoxy, sulfonate, thiosulfonate, silane, alkoxysilane, halos lane, and phosphoramidate. More specific examples of these groups include succinimidyl ester or carbonate, imidazolyl ester or carbonate, benzotriazole ester or carbonate, p-nitrophenyl carbonate, vinyl sulfone, chloroethylsulfone, vinylpyridine, pyridyl disulfide, iodoacetamide, glyoxal, dione, mesylate, tosylate, and tresylate. Also included are other activated carboxylic acid derivatives, as well as hydrates or protected derivatives of any of the above moieties (e.g. aldehyde hydrate, hemiacetal, acetal, ketone hydrate, hemiketal, ketal, thioketal, thioacetal). Preferred electrophilic groups include succinimidyl carbonate, succinimidyl ester, maleimide, benzotriazole carbonate, glycidyl ether, imidazoyl ester, p-nitrophenyl carbonate, acrylate, tresylate, aldehyde, and orthopyridyl disulfide.

Representative examples of reaction sequences by which PEO- and PPO-containing block copolymers can be end-functionalized are provided below.

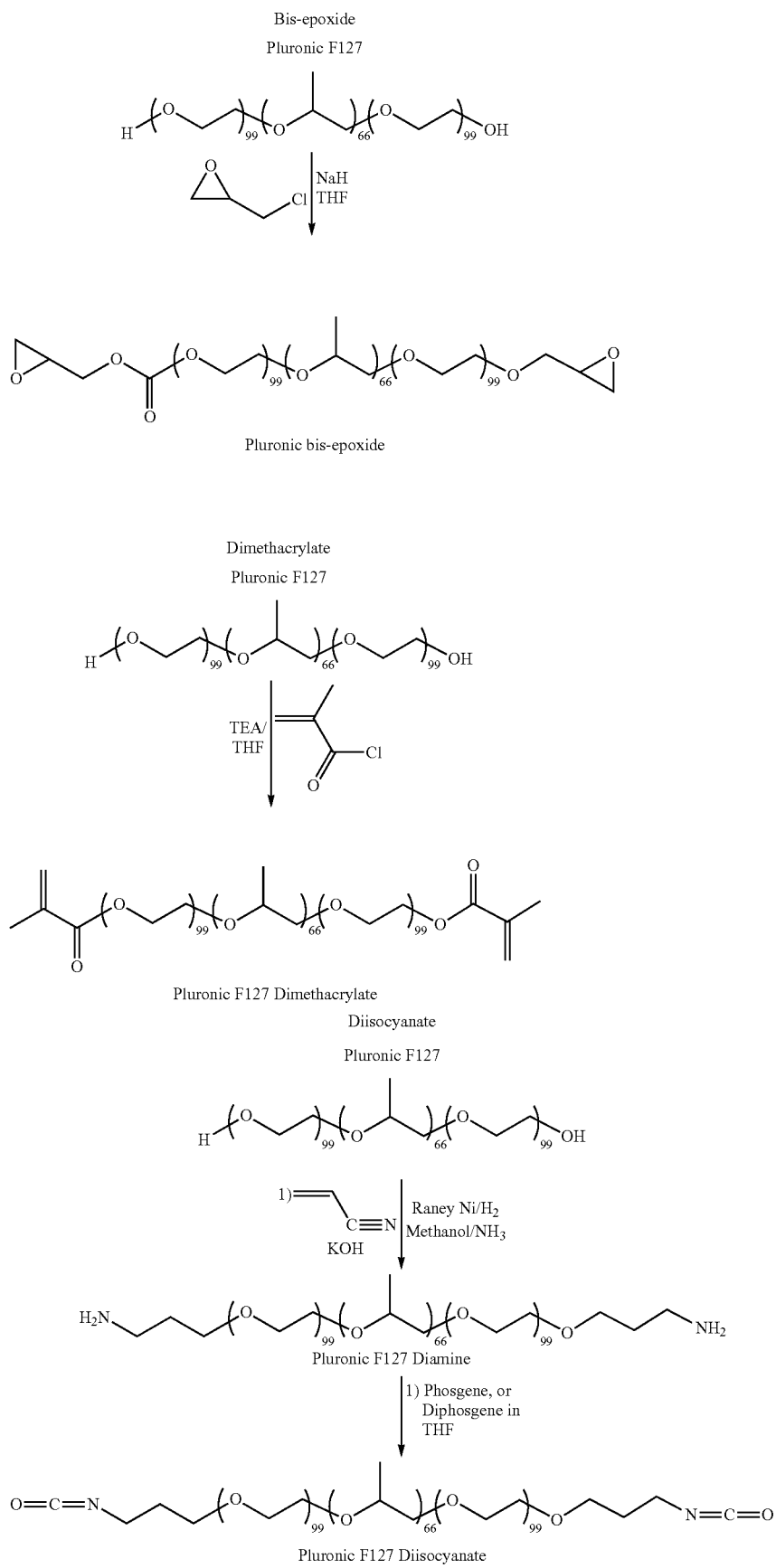

Further provided herein are certain exemplary, but non-limiting, examples of reactions for providing functionalized termini or PEO- and PPO-containing block copolymers. It is to be understood that one of ordinary skill in the art would be able to determine other reaction methods without engaging in an undue amount of experimentation. It should also be understood that any particular block copolymer molecule shown is only one chain length of a polydispersed population of the referenced material.

PEO- and PPO-containing block copolymers are presently preferred. An example of such a copolymer that can be used with the method of the invention is Pluronic® F127, a block copolymer having the structure [(polyethylene oxide)$_{99}$-(polypropylene oxide)$_{66}$-(polyethylene oxide)$_{99}$]. The terminal hydroxyl groups of the copolymer are functionalized to allow for the reaction of the copolymer with other ophthalmic device forming monomers.

In one embodiment, an end terminal functionalized surfactant is selected from the group consisting of poloxamers having at least one end terminal functionalized, reverse poloxamers having at least one end terminal functionalized, poloxamines having at least one end terminal functionalized, reverse poloxamines having at least one end terminal functionalized and mixtures thereof.

Generally, the end terminal functionalized surfactants will be present in the monomeric mixtures in an amount ranging from about 0.01 to about 20 weight percent, preferably from about 1 to about 10 weight percent, and most preferably from about 3 to about 6 weight percent, based on the total weight of the mixture.

The monomeric mixture may further contain, as necessary and within limits not to impair the purpose and effect of the present invention, various additives such as an antioxidant, coloring agent, ultraviolet absorber, lubricant internal wetting agents, toughening agents and the like and other constituents as is well known in the art.

The polymerization products disclosed herein can be obtained by polymerizing the monomer mixture by conventional techniques for polymerization, typically thermal or photochemical polymerization. For thermal polymerization, a temperature from about 40° C. to about 120° C. is used. For photochemical polymerization, radiation such as gamma, ultraviolet (UV), visible, or microwave radiation may be used.

Polymerization is generally performed in a reaction medium, such as, for example, a solution or dispersion using a solvent, e.g., water or an alkanol containing from 1 to 4 carbon atoms such as methanol, ethanol or propan-2-ol. Alternatively, a mixture of any of the above solvents may be used.

A polymerization initiator may be included in the mixture to facilitate the polymerization step. Representative free radical thermal polymerization initiators are organic peroxides such as, for example, acetal peroxide, lauroyl peroxide, decanoyl peroxide, stearoyl peroxide, benzoyl peroxide, tertiarylbutyl peroxypivalate, peroxydicarbonate, and the like and mixtures thereof. Representative UV initiators are those known in the field such as, for example, benzoin methyl ether, benzoin ethyl ether, Darocure 1173, 1164, 2273, 1116, 2959, 3331 (EM Industries) and Igracure 651 and 184 (Ciba-Geigy), and the like and mixtures thereof. Generally, the initiator will be employed in the monomeric mixture at a concentration at about 0.1 to about 5 percent by weight of the total mixture.

Generally, polymerization can be carried out for about 15 minutes to about 72 hours, and under an inert atmosphere of, for example, nitrogen or argon. If desired, the resulting polymerization product can be dried under vacuum, e.g., for about 5 to about 72 hours or left in an aqueous solution prior to use.

When carrying out polymerization, it is particularly advantageous to polymerize the monomeric mixture against a hydrophobic substrate. Useful hydrophobic substrates include, but are not limited to, polypropylene, polystyrene, silanized glass and the like and combinations thereof. Although the inventors do not wish to be bound by any particular theory, it is believed that by casting the polymerization product against a hydrophobic substrate, the hydrophobic monomer(s) in the monomer mixture will migrate towards the hydrophobic substrate and form an evaporative dehydration barrier layer on the top surface of the ophthalmic device thus obtained. The evaporative dehydration barrier layer may not only prevent the water in the high content ophthalmic device of the present invention from evaporating and thereby leaving the device but also prevent the water in the cornea from leaving the cornea to replace the water in the device. This would therefore allow the device to retain its initial water content more effectively and substantially reduce the extraction of water from the corneal surface. Accordingly, in one embodiment, the ophthalmic devices of the present invention exhibit a dehydration rate of less than or equal to about 0.600 mg/minute. In another embodiment, the ophthalmic devices of the present invention exhibit a dehydration rate of less than or equal to about 0.544 mg/minute. In yet another embodiment, the ophthalmic devices of the present invention exhibit a dehydration rate of less than or equal to about 0.450 mg/minute.

In another embodiment, the evaporative dehydration barrier layer of the ophthalmic devices of the present invention can have a contact angle of about 20 to about 150 and preferably from about 50 to about 90. The contact angles of the evaporative dehydration barrier layer of the ophthalmic device can be determined according to the Sessile Drop Method as expanded upon by Zisman et al., *J. Colloid Sci.*, Vol. 1, p. 513 (1946). In the method, the ophthalmic device is placed on a flat plate in a goniometer such as a Rane-Hart. Next, a drop of liquid of interest (e.g., distilled water, buffered saline or any other probe liquid of interest) is applied to the device through a metered syringe. The angle can be read from the viewer, after adjusting the baseline.

As one skilled in the art would readily appreciate, other methods for determining contact angles known in the art can also be employed. Representative examples of such methods for determining a contact angle include an expanded sessile drop technique using multiple liquids of homologous series to generate Zisman plots to obtain the critical surface tension, or theta condition that is determined from a Baier plot of bioadhesion; dynamic contact angles based on the Wilhelmy plate technique; and the captive bubble technique in which the contact angle is of an air bubble at the interface between the solid test surface and a chosen liquid medium. Generally, the contact angle at an interface is dependent on the solid-liquid-gas interface, and is dependent on the properties of all three. Hence, a contact angle for a solid test material can greatly change by a change in the choice of the liquid, such as a change from distilled water to borate buffered saline. For the sake of the example herein disclosed, the liquid medium is fixed and the solid test surface has a change in the surface from one layer to the next. Such a measure of hydrophilicity is indicated when using a liquid for the contact angle analysis that is hydrophilic, so that a reduced contact angle on the surface is indicative of a decreased hydrophobicity and thus an increased hydrophilicity. Additionally, various analytical techniques such as angle dependent X-ray photoelectron spectroscopy (AD-XPS), or Time of Flight-Secondary Ion Mass Spectroscopy (TOF-SIMS) may be used to probe the surface confirm that the evaporative dehydration barrier layer is present on the surface of the ophthalmic device.

The ophthalmic device such as a contact lens of the present invention may be subjected to optional machining operations. For example, the optional machining steps may include buffing or polishing a lens edge and/or surface. Generally, such machining processes may be performed before or after the product is released from a mold part, e.g., the lens is dry released from the mold by employing vacuum tweezers to lift the lens from the mold, after which the lens is transferred by means of mechanical tweezers to a second set of vacuum tweezers and placed against a rotating surface to smooth the surface or edges. The lens may then be turned over in order to machine the other side of the lens.

The lens may then be transferred to individual lens packages containing a buffered saline solution. The saline solution may be added to the package either before or after transfer of the lens. Appropriate packaging designs and materials are known in the art. A plastic package is releasably sealed with a film. Suitable sealing films are known in the art and include foils, polymer films and mixtures thereof. The sealed packages containing the lenses are then sterilized to ensure a sterile product. Suitable sterilization means and conditions are known in the art and include, for example, autoclaving.

As one skilled in the art will readily appreciate, other steps may be included in the molding and packaging process described above. Such other steps can include, for example, coating the formed lens, surface treating the lens during formation (e.g., via mold transfer), inspecting the lens, discarding defective lenses, cleaning the mold halves, reusing the mold halves, and the like and combinations thereof.

The following examples are provided to enable one skilled in the art to practice the invention and are merely illustrative of the invention. The examples should not be read as limiting the scope of the invention as defined in the claims.

EXAMPLE 1

A monomer mixture was prepared by mixing the following components, N-vinyl-2-pyrrolidone (NVP) (90 weight percent); 4-t-butyl-2-hydroxycyclohexyl methacrylate (TBE) (10 weight percent), Pluronics® F127 dimethacrylate (HLB=22, Mw~12600) (5 weight percent), ethylene glycol dimethacrylate (EGDMA) (0.15 weight percent), allyl methacrylate (AMA) (0.15 weight percent) and 2-hydroxypropylmethacrylate (HEMA) (2 weight percent) and a Vazo 64 initiator (0.5 weight percent). The monomeric mixture was cast in a polypropylene contact lens mold and thermally cured for about 4 hours. The resulting contact lens had an equilibrium water content (EWC) of approximately 82 wt. %, as calculated from the following equation:

$$\left(\frac{\text{(Wet weight (mg)} - \text{Dry weight (mg)}}{\text{Wet weight (mg)}}\right) \times 100$$

The rate of evaporative dehydration for the contact lens was 0.544 mg/min. The rate of dehydration was determined from the slope of the initial linear region of the plot of weight (in mg) versus time as measured by a TA Instruments Q50 Thermal Gravimetric Analyzer (TGA). A disk punched from the center of the lens was placed in the TGA and allowed to dry under an $N_2$ atmosphere while the weight loss was monitored. A comparison of the rate of dehydration for the high water contact lens of Example 1 versus the following currently marketed contact lenses was carried out: (1) balafilcon A contact lens (a commercially available group III extended wear contact lenses from Bausch & Lomb Incorporated of Rochester, N.Y sold under the trade name Purevision®, and having an anionic charge and containing approximately 36% water); (2) a hilafilcon A contact lens (commercially available from Bausch & Lomb Incorporated of Rochester, N.Y., sold under the trade name SofLens® One Day and containing approximately 70% water); and (3) alphafilcon A contact lens (commercially available from Bausch & Lomb Incorporated of Rochester, N.Y., sold under the trade name SofLens® 66 and containing approximately 66% water). The results of the comparison are shown in FIG. 1.

EXAMPLE 2

A monomer mixture as prepared by mixing the following components, NVP (90 weight percent); TBE (10 weight percent) and EGDMA (0.3 weight percent) and a Vazo 64 initiator (0.5 weight percent). To this mixture was added increasing amounts of O-(methacryloxyethyl)-N-(triethoxysilylpropyl) urethane (MTU) up to 15 weight percent.

The monomeric mixture was cast in a polypropylene contact lens mold and thermally cured for about 4 hours. The resulting contact lens had an EWC of approximately 80 wt. %. The rate of evaporative dehydration for the contact lens was 0.416 mg/minute.

EXAMPLE 3

A monomer mixture was prepared by mixing the following components, NVP (90 weight percent); TBE (10 weight percent), EGDMA (0.3 weight percent) Pluronics® F127 dimethacrylate (DM) (HLB=22, Mw~12600) (2 weight percent), and a Vazo 64 initiator (0.5 weight percent). The resultant monomeric mixture was cast in a polypropylene contact lens mold and thermally cured for about 4 hours. The resulting contact lens had an EWC of approximately 80 wt. %.

EXAMPLE 4

A monomer mixture was prepared by mixing the following components, NVP (90 weight percent); TBE (10 weight percent), EGDMA (0.3 weight percent) Pluronics® F127 dimethacrylate (DM) (HLB=22, Mw~12600) (5 weight percent), and a Vazo 64 initiator (0.5 weight percent). The resultant monomeric mixture was cast in a polypropylene contact lens mold and thermally cured for about 4 hours. The resulting contact lens had an EWC of approximately 80 wt. %.

EXAMPLE 5

A monomer mixture was prepared by mixing the following components, NVP (90 weight percent); TBE (10 weight percent), EGDMA (0.3 weight percent Pluronics® F127 dimethacrylate (DM) (HLB=22, Mw~12600) (10 weight percent), and a Vazo 64 initiator (0.5 weight percent). The resultant monomeric mixture was cast in a polypropylene contact lens mold and thermally cured for about 4 hours. The resulting contact lens had an EWC of approximately 80%.

EXAMPLE 6

A monomer mixture was prepared by mixing the following components, NVP (90 weight percent); TBE (10 weight percent), EGDMA (0.15 weight percent), HEMA-vinyl carbamate (HEMA-VC) (0.15 weight percent), Pluronics® F38 dimethacrylate (DM) (HLB=31, Mw~4700) (2 weight percent), and a Vazo 64 initiator (0.5 weight percent). The resultant monomeric mixture was cast in a polypropylene contact lens mold and thermally cured for about 4 hours. The resulting contact lens had an EWC of approximately 80 wt. %.

EXAMPLE 7

A monomer mixture was prepared by mixing the following components, NVP (90 weight percent); TBE (10 weight percent), EGDMA (0.15 weight percent), HEMA-VC (0.15 weight percent), Pluronics® F38 dimethacrylate (DM) (HLB=31, Mw~4700) (5 weight percent), and a Vazo 64 initiator (0.5 weight percent). The resultant monomeric mixture was cast in a polypropylene contact lens mold and thermally cured for about 4 hours. The resulting contact lens had an EWC of approximately 80 wt. %.

EXAMPLE 8

A monomer mixture was prepared by mixing the following components, NVP (90 weight percent); TBE (10 weight percent), EGDMA (0.15 weight percent), HEMA-VC (0.15 weight percent), Pluronics® F38 dimethacrylate (DM) (HLB=31, Mw~4700) (10 weight percent), and a Vazo 64 initiator (0.5 weight percent). The resultant monomeric mixture was cast in a polypropylene contact lens mold and thermally cured for about 4 hours. The resulting contact lens had an EWC of approximately 80 wt. %.

EXAMPLE 9

A monomer mixture was prepared by mixing the following components, NVP (90 weight percent); TBE (10 weight percent), EGDMA (0.15 weight percent), HEMA-VC (0.15 weight percent), Pluronics® F38 dimethacrylate (DM) (HLB=31, Mw~4700) (20 weight percent), and a Vazo 64 initiator (0.5 weight percent). The resultant monomeric mixture was cast in a polypropylene contact lens mold and thermally cured for about 4 hours. The resulting contact lens had an EWC of approximately 80 wt. %.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the features and advantages appended hereto.

What is claimed is:

1. An ophthalmic device that is a polymerization product of a monomeric mixture comprising: (a) a major amount of a non-silicone-containing hydrophilic monomer; (b) a hydrophobic monomer; and (c) a crosslinking agent, wherein the ophthalmic device has an equilibrium water content of at least about 70 weight percent and further wherein the surface of the ophthalmic device substantially inhibits evaporative dehydration.

2. The ophthalmic device of claim 1, having an equilibrium water content of at least about 80 weight percent.

3. The ophthalmic device of claim 1, wherein the non-silicone-containing hydrophilic monomer is selected from the group consisting of an amide, cyclic lactam, poly(alkene glycols) functionalized with polymerizable groups and mixtures thereof.

4. The ophthalmic device of claim 1, wherein the non-silicone-containing hydrophilic monomer is selected from the group consisting of N,N-dimethylacrylamide, N,N-dimethylmethacrylamide, N-vinyl-2-pyrrolidone and mixtures thereof.

5. The ophthalmic device of claim 1, wherein the non-silicone-containing hydrophilic monomer is present in the monomeric mixture in an amount of greater than about 70 weight percent, based on the total weight of the monomeric mixture.

6. The ophthalmic device of claim 1, wherein the non-silicone-containing hydrophilic monomer is present in the monomeric mixture in an amount of greater than about 80 weight percent, based on the total weight of the monomeric mixture.

7. The ophthalmic device of claim 1, wherein the hydrophobic monomer is represented by the structure of Formula I:

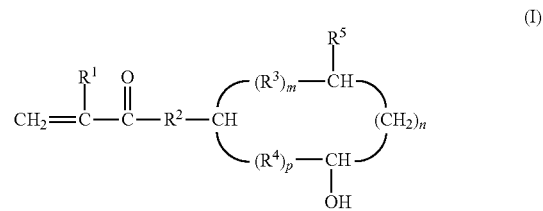

wherein $R^1$ is methyl or hydrogen; $R^2$ is —O— or —NH—; $R^3$ and $R^4$ are independently a divalent radical selected from the group consisting of —CH$_2$—, —CHOH— and —CHR$^6$—; $R^5$ and $R^6$ are independently a branched $C_3$-$C_8$ alkyl group; and n is an integer of at least 1, and m and p are independently 0 or an integer of at least 1, provided that the sum of m, p and n is 2, 3, 4 or 5.

8. The ophthalmic device of claim 1, wherein the hydrophobic monomer is present in the monomeric mixture in an amount of about 0.5 to about 25 weight percent.

9. The ophthalmic device of claim 1, wherein the monomeric mixture further comprises a hydrophobic silicon-containing monomer.

10. The ophthalmic device of claim 9, wherein the hydrophobic silicon-containing monomer is O-(methacryloxyethyl)-N-(triethoxysilylpropyl)urethane.

11. The ophthalmic device of claim 9, wherein the hydrophobic silicon-containing monomer is present in the monomeric mixture in an amount up to about 15 weight percent.

12. The ophthalmic device of claim 1, having a dehydration rate of less than or equal to about 0.600 mg/minute.

13. The ophthalmic device of claim 9, having a dehydration rate of less than or equal to about 0.450 mg/minute.

14. The ophthalmic device of claim 1, wherein the ophthalmic device is a contact lens.

15. A method comprising the step of casting a monomeric mixture comprising (a) a major amount of a non-silicone-containing hydrophilic monomer; (b) a hydrophobic monomer; and (c) a crosslinking agent in a hydrophobic substrate to form an ophthalmic device having an evaporative dehydration barrier layer on the surface thereof and wherein the surface of the ophthalmic device substantially inhibits evaporative dehydration.

16. The method of claim 15, wherein the ophthalmic device has an equilibrium water content of at least about 80 weight percent.

17. The method of claim 15, wherein the ophthalmic device has a dehydration rate of less than or equal to about 0.600 mg/minute.

18. The method of claim 15, wherein the hydrophilic monomer is present in the monomeric mixture in an amount of greater than about 70 weight percent.

19. The method of claim 15, wherein the monomeric mixture further comprises a hydrophobic silicon-containing monomer.

20. The method of claim 15, wherein the hydrophobic substrate comprises polypropylene, polystyrene, silanized glass or a combination thereof.

21. A method for substantially mitigating evaporative corneal dehydration associated with an ophthalmic device having an equilibrium water content of at least about 70 weight percent, the method comprising contacting the surface of an eye of a subject with an ophthalmic device that is a polymerization product of a monomeric mixture comprising: (a) a major amount of a non-silicone-containing hydrophilic monomer; (b) a hydrophobic monomer; and (c) a crosslinking agent, wherein the ophthalmic device has an equilibrium water content of at least about 70 weight percent and further wherein the surface of the ophthalmic device substantially inhibits evaporative dehydration.

* * * * *